United States Patent [19]
Tubo et al.

[11] Patent Number: 5,723,331
[45] Date of Patent: Mar. 3, 1998

[54] METHODS AND COMPOSITIONS FOR THE REPAIR OF ARTICULAR CARTILAGE DEFECTS IN MAMMALS

[75] Inventors: Ross A. Tubo, Quincy; Leesa M. Barone, Winthrop; Courtney A. Wrenn, Haverhill, all of Mass.

[73] Assignee: Genzyme Corporation, Framingham, Mass.

[21] Appl. No.: 469,966

[22] Filed: Jun. 6, 1995

Related U.S. Application Data

[62] Division of Ser. No. 245,565, May 5, 1994, abandoned.

[51] Int. Cl.$^6$ ............................... C12N 5/00; C12N 5/02
[52] U.S. Cl. ..................... 435/366; 435/325; 435/395; 435/397; 424/423; 623/11
[58] Field of Search ..................... 435/240.2, 325, 435/366, 395, 397; 424/423; 514/2, 8; 623/11

[56] References Cited

U.S. PATENT DOCUMENTS 5,206,023  4/1993  Hunziker ............................ 424/423

*Primary Examiner*—Leon B. Lankford, Jr.

[57] ABSTRACT

Provided are methods and compositions for the repair of articular cartilage defects in a mammal. Denuded chondrogenic cells are proliferated ex vivo as monolayer cultures in order to expand the pool of available chondrogenic cells. During proliferation the chondrogenic cells stop secreting the extracellular matrix components, type II collagen and sulfated proteoglycans. The proliferated cells then are seeded into a pre-shaped well having a cell contacting, cell abhesive surface. The cells cultured in the well redifferentiate and begin to secrete cartilage-specific extracellular matrix again. Accordingly, essentially unlimited amounts of synthetic cartilage may be prepared from small samples of biopsy tissue. Also provided are methods for surgically repairing articular cartilage defects in mammals using the synthetic cartilage prepared in accordance with the invention.

15 Claims, 2 Drawing Sheets

METHODS AND COMPOSITIONS FOR THE REPAIR OF ARTICULAR CARTILAGE DEFECTS IN MAMMALS

This is a divisional application Ser. No. 08/245,565 filed on May 5, 1994, now abandoned.

FIELD OF THE INVENTION

This invention relates to methods and compositions for the repair of articular cartilage defects in a mammal. The methods and synthetic cartilage compositions of the invention are particularly useful in treatment of partial-thickness and full-thickness articular cartilage defects.

BACKGROUND OF THE INVENTION

Cartilage is a hyperhydrated structure with water comprising 70% to 80% of its weight. The remaining 20% to 30% comprises type II collagen and proteoglycan. The collagen usually accounts for 70% of the dry weight of cartilage (in "*Pathology*" (1988) Eds. Rubin & Farber, J. B. Lippincott Company, PA. pp. 1369–1371). Proteoglycans are composed of a central protein core from which long chains of polysaccharides extend. These polysaccharides, called glycosaminoglycans, include: chondroitin-4-sulfate; chondroitin-6-sulfate; and keratan sulfate. Cartilage has a characteristic structural organization consisting of chondrogenic cells dispersed within an endogenously produced and secreted extracellular matrix. The cavities in the matrix which contain the chondrocytes are called cartilage lacunae. Unlike bone, cartilage is neither innervated nor penetrated by either the vascular or lymphatic systems (Clemente (1984) in "*Gray's Anatomy, 30th Edit,*" Lea & Febiger).

Three types of cartilage are present in a mammal and include: hyaline cartilage; fibrocartilage and elastic cartilage (Rubin and Farber, supra). Hyaline cartilage consists of a gristly mass having a firm, elastic consistency, is translucent and is pearly blue in color. Hyaline cartilage is predominantly found on the articulating surfaces of articulating joints. It is found also in epiphyseal plates, costal cartilage, tracheal cartilage, bronchial cartilage and nasal cartilage. Fibrocartilage is essentially the same as hyaline cartilage except that it contains fibrils of type I collagen that add tensile strength to the cartilage. The collagenous fibers are arranged in bundles, with the cartilage cells located between the bundles. Fibrocartilage is found commonly in the anulus fibrosus of the invertebral disc, tendinous and ligamentous insertions, menisci, the symphysis pubis, and insertions of joint capsules. Elastic cartilage also is similar to hyaline cartilage except that it contains fibers of elastin. It is more opaque than hyaline cartilage and is more flexible and pliant. These characteristics are defined in part by the elastic fibers embedded in the cartilage matrix. Typically, elastic cartilage is present in the pinna of the ears, the epiglottis, and the larynx.

The surfaces of articulating bones in mammalian joints are covered with articular cartilage. The articular cartilage direct contact of the opposing bone surfaces and the near frictionless movement of the articulating bones relative to one another (Clemente, supra).

Two types of articular cartilage defects are commonly observed in mammals and include full-thickness and partial-thickness defects. The two-types of defects differ not only in the extent of physical damage but also in the nature of repair response each type of lesion elicits.

Full-thickness articular cartilage defects include damage to the articular cartilage, the underlying subchondral bone tissue, and the calcified layer of cartilage located between the articular cartilage and the subchondral bone. Full-thickness defects typically arise during severe trauma of the joint or during the late stages of degenerative joint diseases, for example, during osteoarthritis. Since the subchondral bone tissue is both innervated and vascularized, damage to this tissue is often painful. The repair reaction induced by damage to the subchondral bone usually results in the formation of fibrocartilage at the site of the full-thickness defect. Fibrocartilage, however, lacks the biomechanical properties of articular cartilage and fails to persist in the joint on a long term basis.

Partial-thickness articular cartilage defects are restricted to the cartilage tissue itself. These defects usually include fissures or clefts in the articulating surface of the cartilage. Partial-thickness defects are caused by mechanical derangements of the joint which in turn induce wearing of the cartilage tissue within the joint. In the absence of innervation and vasculature, partial-thickness defects do not elicit repair responses and therefore tend not to heal. Although painless, partial-thickness defects often degenerate into full-thickness defects.

Repair of articular cartilage defects with suspensions of isolated chondrocytes has been attempted in a variety of animal models. See for example: Bentley, et al. (1971) *Nature* 230:385–388; Langer et al. (1974) *J. Bone Joint Surg.* 56-A:297–304; Green (1977) *Clin. Orthop.* 124:237–250; and Aston et al. (1986) *J. Bone Joint Surg.* 68-B:29–35). During transplantation, the cell suspensions may be retained in the defect behind a piece of periosteal tissue that has been previously attached to the surface of the normal cartilage tissue. The rate of successful implantation using cell suspensions was found to be about 40%. It is believed that chondrocytes transplanted in this manner lose their viability during transplantation and that the procedure may result in the formation of fibrocartilage or islands of cartilage embedded in fibrous tissue at the site of the defect.

Three alternative approaches have been developed in an attempt to improve the success rate in treating mammalian articular cartilage defects. In the first approach, synthetic carrier matrices containing dispersed allogeneic chondrocytes may be implanted into the cartilage defect. The implanted chondrocytes hopefully produce and secrete components of the extracellular matrix thereby to form articular cartilage at the site of the defect in situ. In the second approach, synthetic carrier matrices containing chemotactic and mitogenic growth factors may be implanted into the cartilage defect. The growth factors hopefully induce the influx into, and the proliferation of chondrocyte progenitor cells within the matrix. The chondrocyte progenitor cells differentiate subsequently into chondrocytes that in turn secrete components of the extracellular matrix thereby to form articular cartilage at the site of the defect in situ. In the third approach, synthetic cartilage tissue may be grown in vitro and implanted subsequently into the cartilage defect.

In the first approach, the synthetic matrices or biological resorbable immobilization vehicles may be impregnated with allogeneic chondrocytes. A variety of synthetic carrier matrices have been used to date and include: three-dimensional collagen gels (U.S. Pat. No. 4,846,835; Nishimoto (1990) *Med. J. Kinki University* 15; 75–86; Nixon et al. (1993) *Am. J. Vet. Res.* 54:349–356; Wakitani et al. (1989) *J. Bone Joint Surg.* 71B:74–80; Yasui (1989) *J. Jpn. Ortho. Assoc.* 63:529–538); reconstituted fibrin-thrombin gels (U.S. Pat. Nos. 4,642,120; 5,053,050 and 4,904,259); synthetic polymer matrices containing polyanhydride, polyorthoester, polyglycolic acid and copolymers thereof (U.S. Pat. No. 5,041,138); and hyaluronic acid-based polymers (Robinson et al. (1990) *Calcif. Tissue Int.* 46:246-253).

The introduction of non-autologous materials into a patient, however, may stimulate an undesirable immune response directed against the implanted material. Such an immune response has been observed in rabbit models (Yoshinao (1990) *J. Jpn. Orth. Assoc.* 64:835-846. In addition, there is evidence to suggest that neo-cartilage may be formed around the periphery of the implant thereby preventing integration of the implant into the cartilage defect. See for example, Messner (1994) 40$^{th}$ *Annual Meeting Orth. Res. Soc.*, New Orleans p. 239; and Nixon et al. (1994) 40$^{th}$ *Annual Meeting Orth. Res. Soc.*, New Orleans p. 241. Monitoring the formation and development of the resulting synthetic cartilage in situ can be difficult to perform and usually involves an arthroscopic or open joint examination. Furthermore, implants containing synthetic polymer components may be unsuitable for repairing large cartilage defects since polymer hydrolysis in situ may inhibit the formation of cartilage and/or its integration into the defect.

In the second approach, the defect may be filled with a biocompatible, biodegradable matrix containing growth factors to stimulate the influx of chondrocyte progenitor cells into the matrix in situ. The matrices optimally contain pores of sufficient dimensions to permit the influx into, and proliferation of the chondrocyte progenitor within the matrix. The matrix also may contain differentiating growth factors to stimulate the differentiation of chondrocyte progenitor cells into chondrocytes. The resulting chondrocytes hopefully secrete extracellular matrix components thereby to form cartilage at the site of the defect in situ. See for example, U.S. Pat. Nos. 5,206,023; 5,270,300; and EP 05 30 804 A1. This approach, however, may have problems similar to those associated with the first approach, hereinabove.

In the third approach, chondrocytes may be cultured in vitro thereby to form synthetic cartilage-like material. The resulting cartilage may be implanted subsequently into the cartilage defect. This type of approach has the advantage over the previous methods in that the development of the synthetic cartilage material may be monitored prior to implantation. In addition, the resulting cartilage may be characterized biochemically and morphologically prior to implantation. Two general procedures have been developed for growing synthetic cartilage in vitro. These include growing chondrogenic cells in either an anchorage-dependent or an anchorage-independent manner.

In the anchorage-independent manner, the chondrogenic cells may be cultured as colonies within an agarose gel. See for example: Benya et al. (1982) *Cell* 30:215-224; Aydlotte et al. (1990) in *Methods and Cartilage Research* Chapter 23:pp. 90-92; Aulthouse et al. (1989) *In Vitro Cellular and Developmental Biology* 25:659-668; Delbruck et al. (1986) *Connective Tissue Res.* 15:1550-172; and Bohme et al. (1992) *J. Cell Biol.* 116:1035-1042. Heretofore, only small pieces of cartilage tissue of undefined shape have been prepared using this approach. Furthermore, the resulting cartilage remains embedded within a gel matrix making it unsuitable for implantation into mammals. Alternatively, in another anchorage-independent method, chondrocytes may be cultured as colonies in suspension culture. See for example, Franchimont et al. (1989) *J. Rheumatol.* 16:5-9; and Bassleer et al. (1990) in *"Methods and Cartilage Research"*, Academic Press Ltd., Chapter 24. As with the gel approach, the resulting particles containing synthethic cartilage-like material may be small and of undefined shape thus making the particles unsuitable for implantation and repair of a predetermined articular cartilage defect.

In the anchorage-dependent method, primary cultures of chondrogenic cells isolated from primary tissue may be grown as monolayers attached to the surface of a cell culture flask. See for example: Yoshihashi (1983) *J. Jpn. Ortho. Assoc.* 58:629-641; and U.S. Pat. No. 4,356,261. The primary cells derived directly from explant tissue remain capable of producing and secreting extracellular components characteristic of natural cartilage, specifically, type II collagen and sulfated proteoglycans. However, it was observed that after passaging and proliferating the cells as monolayers, by serially passaging the cells, the cells dedifferentiate and lose their ability to secrete type II collagen and sulfated proteoglycans (Schlitz et al., (1973) *Cell Differentiation* 1:97-108; Mayne et al. (1975) *Proc. Natl. Acad. Sci. USA* 72:4511-4515; Mayne et al. (1976) *Proc. Natl. Acad. Sci. USA* 73:1674-1678; Okayama et al. (1976) *Proc. Natl. Acad. Sci. USA* 73:3224-3228; Pacifici & Holtzer (1977) *Am. J. Anat.* 150:207-212; Pacifici et al. (1977) *Cell* 11:891-899; West et al. (1979) *Cell* 17:491-501; von der Mark (1980) *Curr. Top. Dev. Biol.* 14:199-225; Oegama and Thompson (1981) *J. Biol. Chem.* 256:1015-1022; Benya & Schaffer, supra). Consequently, until now it has not been possible to prepare large patches of articular cartilage from small pieces of biopsy tissue using the anchorage-dependent procedures disclosed in U.S. Pat. No. 4,356,261 and Yoshihashi (supra) since the chondrocytes, following the proliferation as monolayers, dedifferentiate and stop secreting a cartilage-specific extracellular matrix.

It is an object of the invention to provide a variety of methods and compositions for the repair of articular cartilage defects in a mammal. Specifically, it is an object of the invention to provide a method for preparing in vitro large quantities of synthetic cartilage from small samples of biopsy tissue for the repair of articular cartilage defects in a mammal. The proliferated but undifferentiated chondrogenic cells may be cultured under conditions that stimulate the secretion of extracellular components characteristic of cartilage. Another object is to provide a method for producing a patch of synthetic cartilage of predetermined volume in vitro. Yet another object is to provide methodologies for preparing synthetic cartilage from chondrocytes isolated from a variety of tissues including pre-existing cartilage tissue and perichondrial tissue. Still another object is to provide methodologies for the repair of articular cartilage defects in a mammal using the compositions described herein.

These and other objects and features of the invention will be apparent from the description, drawings, and claims which follow.

SUMMARY OF THE INVENTION

It has been discovered that large quantities of three-dimensional, multi cell-layered synthetic cartilage may be prepared in vitro from small biopsy samples by the practice of the invention described herein. Also, it has been discovered that synthetic cartilage patches of pre-determined volume may be prepared in vitro by culturing chondrogenic cells in an anchorage-independent manner in a pre-shaped well. Furthermore, it has been discovered that chondrogenic cells useful in the practice of the instant invention may be isolated from a variety of tissues, for example: pre-existing cartilage; perichondrial tissue; or bone marrow, and expanded in vitro prior to cartilage formation. These discoveries enable the preparation of patches of synthetic cartilage for the repair of articular cartilage defects in a mammalian joint.

Broadly, the invention comprises a method for preparing in vitro a synthetic cartilage patch for the repair of a cartilage defect in a mammal. The method includes: (1) seeding denuded chondrogenic cells, proliferated ex vivo, into a pre-shaped well having a cell contacting, cell abhesive surface; and (2) culturing the proliferated chondrogenic cells in the well for a time sufficient to permit the cells to secrete an extracellular matrix thereby to form a three-dimensional, multi cell-layered patch of synthetic cartilage. The resulting synthetic cartilage, preferably synthetic articular cartilage, contains chondrogenic cells dispersed within an endogenously produced and secreted extracellular matrix. The resulting synthetic cartilage patch may be used subsequently for the repair of an articular cartilage defect in a mammal.

As used herein, the term "synthetic cartilage", is understood to mean any cartilage tissue produced in vitro that contains chondrogenic cells dispersed within an endogenously produced and secreted extracellular matrix. The extracellular matrix is composed of collagen fibrils (predominantly fibrils of type II collagen), sulfated proteoglycans, for example, chondroitin-6-sulfate and keratan sulfate, and water.

As used herein, the term "synthetic articular cartilage", is understood to mean any cartilage tissue produced in vitro that biochemically and morphologically resembles the cartilage normally found on the articulating surfaces of mammalian joints.

As used herein, the term "chondrogenic cell", is understood to mean any cell which, when exposed to an appropriate stimuli, may differentiate into a cell capable of producing and secreting components characteristic of cartilage tissue, for example, fibrils of type II collagen, and the sulfated proteoglycans, chondroitin-6-sulfate and keratan sulfate.

As used herein, the term "denuded cell" is understood to mean any cell that has been isolated from a disaggregated tissue containing such a cell. The tissue of interest may be enzymatically and/or mechanically disaggregated in order to release the denuded cells.

As mentioned hereinabove, the cells are cultured in a pre-shaped well having a cell contacting, cell abhesive surface. The cell abhesive surface discourages the chondrogenic cells from attaching to the cell contacting surface of the well. The use of such a well having a cell contacting, cell abhesive surface is a critical aspect of the instant invention. Heretofore, it has been observed that chondrogenic cells expanded by serially passaging the cells as monolayers usually lose their ability to secrete type II collagen and sulfated proteoglycans. It now has been discovered that the undifferentiated, proliferated chondrogenic cells when cultured in such a well redifferentiate and once again start to secrete cartilage specific type II collagen and sulfated proteoglycans.

It is contemplated that the actual dimensions of the well may be pre-determined when the actual size and shape of the cartilage defect to be repaired is known. For example, the well may be dimensioned such that the resulting cartilage may interfit directly into the cartilage defect. Alternatively, the synthetic cartilage patch may be "trimmed" mechanically to the appropriate size and shape by the surgeon prior to insertion into the defect during a surgical procedure. It is appreciated that synthetic cartilage patches prepared in such a manner have the additional advantage over patches prepared as anchorage-dependent primary explant cultures in that the patches may be easily removed from the well obviating the use of enzymatic or other mechanical procedures. Such procedures may affect deleteriously the biochemical and/or biomechanical properties of the resulting cartilage patch.

Cell abhesive surfaces may be prepared by coating the cell contacting surface of a well with a reagent that discourages cell attachment. Preferred reagents include, but are not limited to, silicon based reagents, for example, dichlorodimethylsilane or polytetrafluoroethylene based reagents, for example, Teflon®. Alternatively, the well may be cast in a material that naturally discourages the attachment of chondrogenic cells. Preferred materials include, but are not limited to, agarose, glass, untreated cell culture plastic and polytetrafluoroethylene, for example, Teflon®. It is contemplated that any biocompatible material or coating capable of discouraging the attachment of chondrogenic cells may be useful in the practice of the instant invention.

Chondrogenic cells useful in the practice of the invention may be isolated from essentially any tissue containing chondrogenic cells. For example, the chondrogenic cells may be isolated directly from pre-existing cartilage tissue, for example, hyaline cartilage, elastic cartilage, or fibrocartilage. Specifically, chondrogenic cells may be isolated from articular cartilage (from either weight bearing or non-weight bearing joints), costal cartilage, nasal cartilage, auricular cartilage, tracheal cartilage, epiglottic cartilage, thyroid cartilage, arytenoid cartilage and cricoid cartilage. Methods for isolating chondrogenic cells from such tissues are set forth hereinbelow. Alternatively, chondrogenic cells may be isolated from bone marrow. See for example, U.S. Pat. Nos. 5,197,985 and 4,642,120, and Wakitani et al. (1994) *J. Bone Joint Surg.* 76:579–591, the disclosures of which are incorporated by reference herein.

Once chondrogenic cells have been isolated from the pre-existing tissue they are proliferated ex vivo in monolayer culture using conventional techniques well known in the art. See for example, Pollack (1975) in "*Readings in Mammalian Cell Culture*", Cold Spring Harbor Laboratory Press, Cold Spring Harbor, the disclosure of which is incorporated by reference herein. Briefly, the population of chondrogenic cells is expanded by culturing the cells as monolayers and by serially passaging the cells. The chondrogenic cells are passaged after the cells have proliferated to such a density that they contact one another on the surface of the cell culture plate. During the passaging step, the cells are released from the substratum. This is performed routinely by pouring a solution containing a proteolytic enzyme, i.e, trypsin, onto the monolayer. The proteolytic enzyme hydrolyzes proteins which anchor the cells on the substratum. As a result, the cells are released from the surface of the substratum. The resulting cells, now in suspension, are diluted with culture medium and replated into a new tissue culture dish at a cell density such that the cells do not contact one another. The cells subsequently reattach onto the surface of the tissue culture and start to proliferate once again. Alternatively, the cells in suspension may be cryopreserved for subsequent use using techniques well known in the art. See for example, Pollack (supra).

The cells are repeatedly passaged until enough cells have been propagated to prepare a piece of synthetic cartilage of pre-determined size. As a result, a population containing a small number of chondrogenic cells originally isolated from a biopsy sample may be expanded in vitro thereby to generate a large number of chondrogenic cells for subsequent use in the practice of the invention.

Following proliferative expansion, the chondrogenic cells are enzymatically released from the substratum to provide a suspension of cells. The cells in suspension then are diluted by the addition of cell culture medium to give a cell density of about $1\times10^5$–$1\times10^9$ proliferated chondrogenic cells per ml, or more preferably about $1\times10^6$–$5\times10^8$ cells per ml, and most preferably about $3 \times 10^6$–$2 \times 10^8$ cells per ml. The cells then are seeded into the pre-shaped well having a cell contacting, cell abhesive surface. About, $1 \times 10^3$–$1 \times 10^7$ cells, preferably $1 \times 10^4$–$1 \times 10^6$ cells, and most preferably about $5 \times 10^4$–$5 \times 10^5$ cells produce a piece of synthetic cartilage 1 mm$^3$ in volume. Accordingly, the artisan may produce a patch of synthetic cartilage of pre-determined size by seeding an appropriate number of chondrogenic cells into a pre-shaped well. The cells subsequently are cultured in the well under conventional cell culture conditions well known in the art from 1 to 90 days, preferably 5 to 60 days, and most preferably 10 to 30 days thereby to induce the production and secretion of extracellular matrix. The present invention therefore enables the production of large quantities of synthetic cartilage patches from small pieces of biopsied tissue.

In a preferred embodiment, the chondrogenic cells, once proliferated ex vivo, may be seeded into a preshaped well dimensioned to determine the volume of the resulting cartilage tissue. Therefore, using the methodologies described herein, one skilled in the art may prepare synthetic cartilage of pre-determined volume for the repair of articular cartilage defects of pre-determined volume.

In another preferred embodiment, polypeptide growth factors may be added to the chondrogenic cells in the pre-shaped well to enhance or stimulate the production of cartilage specific proteoglycans and/or collagen. Preferred growth factors include, but are not limited to, transforming growth factor-$\beta$ (TGF-$\beta$), insulin-like growth factor (IGF), platelet derived growth factor (PDGF), epidermal growth factor (EGF), acidic or basic fibroblast growth factor (aFBF or bFBF), hepatocytic growth factor (HGF), keratinocyte growth factor (KGF) the bone morphogenic factors (BMPs) including: BMP-1; BMP-2; BMP-3; BMP-4; BMP-5; and BMP-6 and the osteogenic proteins (OPs) including: OP-1; OP-2; and OP-3. In addition, it is contemplated that ascorbate may be added to the chondrogenic cells in the pre-shaped well to enhance or stimulate the production of cartilage specific proteoglycans and collagen. However, these particular compounds are not limiting. Any compound or composition capable of stimulating or inducing the production of cartilage specific proteoglycans and collagen may be useful in the practice of the instant invention.

The invention also provides methodologies for effecting the re of an articular cartilage at a pre-determined site in a mammal. The method comprises the steps of: (1) surgically implanting at the pre-determined site a piece of synthetic cartilage prepared by the methodologies described herein; and (2) permitting the synthetic cartilage to integrate into the pre-determined site. The synthetic cartilage patch may be fixed in place during the surgical procedure. This may be effected by surgically fixing the patch with sutures and/or by applying a biocompatible, bioadhesive to the surface interfacing the cartilage patch and the defect. In some instances, defective cartilage tissue may be removed prior to implantation. Although the shape of the synthetic cartilage may be dimensioned to interfit with the cartilage defect, in specific instances, for example, when the defect is large, it is contemplated that a plurality of synthetic cartilage patches may be surgically implanted into the defect.

In another preferred embodiment, the resulting synthetic cartilage patch is preferably allogenic, and more preferably autogenic in nature. Accordingly, synthetic allogenic cartilage may be prepared from biopsy tissue isolated from a mammal belonging to the same species as the recipient. Synthetic autogenic cartilage may be prepared from biopsy tissue derived from the intended recipient. In another preferred embodiment, the invention provides synthetic articular cartilage for the repair articular cartilage defects in humans. Accordingly, chondrogenic cells may be isolated from human cartilage tissue,i.e., human articular cartilage (from weight bearing and non-weight bearing joints), human costal cartilage, human nasal cartilage, human auricular cartilage, human tracheal cartilage, human epiglottic cartilage, human thyroid cartilage, human arytenoid-cartilage and human cricoid cartilage. Alternatively, the chondrogenic cells useful in the practice of the invention may be derived from human bone marrow.

The methodologies described herein are useful in the treatment of both partial-thickness and full-thickness defects of articular cartilage.

BRIEF DESCRIPTION OF THE DRAWINGS

The foregoing and other objects and features of the invention, as well as the invention itself, may be more fully understood from the following description, when read together with the accompanying drawings, in which.

DETAIL DESCRIPTION OF THE INVENTION

It has been discovered that chondrogenic cells sampled from a mammal and proliferated in monolayer culture ex vivo may be cultured further in a pre-shaped well having a cell contacting, cell abhesive surface thereby to generate a three-dimensional, multi cell-layered patch of synthetic cartilage. In addition, it has been discovered that synthetic cartilage patches of pre-determined volume for use in the surgical replacement of damaged articular cartilage and subsequent integration into the joint of the recipient may be prepared in accordance with the invention. Also, it has been discovered that chondrogenic cells useful in the practice of the instant invention may be isolated from a variety of pre-existing tissues, for example, cartilage tissue and perichondrial tissue or alternatively from bone marrow. These discoveries enable preparation of potentially unlimited quantities of synthetic cartilage patches of pre-determined thickness or volume and thus provides a significant advance in the repair of articular cartilage defects in a mammal.

Figure 1:
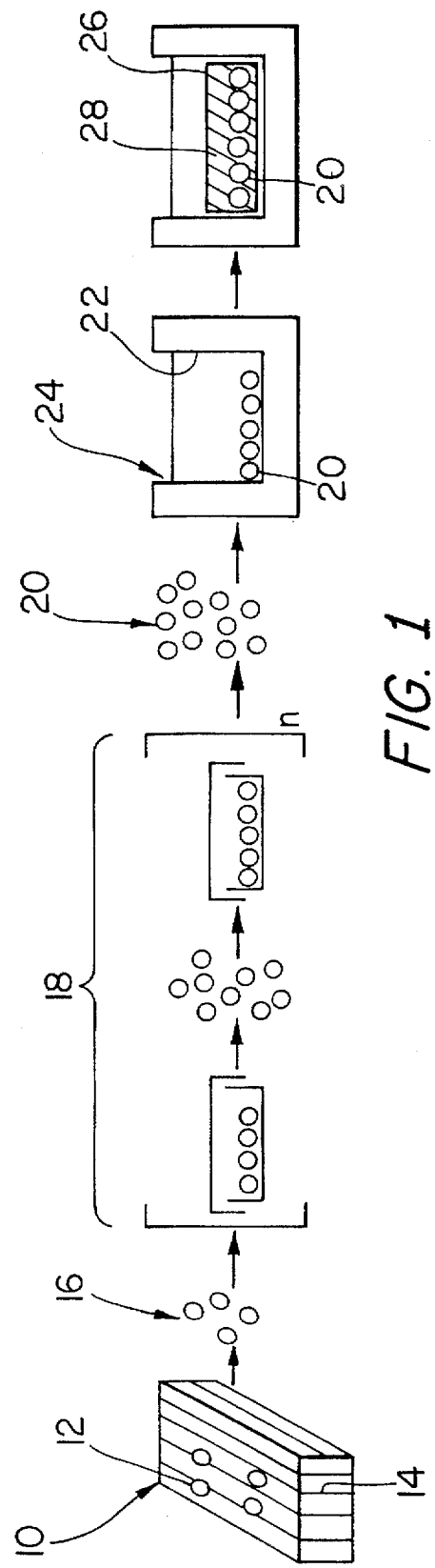
FIG. 1 shows a flow chart summarizing the steps in the preparation of large amounts of synthetic cartilage from small samples of biopsy tissue for the repair of cartilage defects in a mammal. Initially, tissue containing chondrogenic cells is disaggregated to release denuded chondrogenic cells. The isolated, cells then are proliferated by serially culturing and passaging the cells in monolayer culture. During monolayer culture the chondrogenic cells dedifferentiate and lose their ability to secrete cartilage specific extracellular matrix. Once the appropriate number of cells have been obtained, the proliferated cells are seeded into a pre-shaped well having a cell contacting, cell abhesive surface. The chondrogenic cells are cultured in the well for a time sufficient to allow them to redifferentiate and secrete a cartilage specific extracellular matrix thereby to form synthetic cartilage in vitro.

A flow chart summarizing the steps associated with the preparation of three-dimensional, multi cell-layered patches of synthetic cartilage is shown in FIG. 1. All of the steps described hereinbelow are preferably performed under aseptic conditions.

Briefly, tissue (10) containing chondrogenic cells (12) is disaggregated to release denuded chondrogenic cells (16)

from their extracellular matrix (14). The denuded cells then are isolated and proliferated as monolayers in an undifferentiated state ex vivo (18). The passaging procedure may be repeated multiple times (n), for example up to about 7 to 10 passages until enough cells have been propagated to prepare a piece of cartilage of pre-determined size. These steps expand the number of chondrogenic cells in a population that can be used subsequently to form the three-dimensional, multi cell-layered patch of synthetic cartilage.

The proliferated but undifferentiated chondrogenic cells (20) then are seeded into a pre-shaped well (24) having a cell contacting, cell abhesive surface (22). The cell abhesive surface prevents chondrogenic cells cultured in the well from attaching to the surface of the well. The cells, deprived of anchorage, interact with one another and coalesce within hours to generate a cohesive plug of cells. The chondrogenic cells then begin to differentiate, as characterized by the production and secretion of cartilage-specific markers, i.e., type II collagen and sulfated proteoglycans. Type II collagen is found specifically in cartilage. The chondrogenic cells then are cultured in the well for time sufficient to permit the formation of a three-dimensional, multi cell-layered patch of synthetic cartilage (26). The resulting synthetic cartilage patch comprises chondrogenic cells (20) dispersed with a new, endogenously produced and secreted extracellular matrix (28). The extracellular matrix deposited during this procedure is biochemically and morphologically similar to the extracellular matrix found in natural cartilage. Specifically, the synthetic matrix comprises fibers of type II collagen, and sulfated proteoglycans such as chondroitin sulfate and keratan sulfate.

Figure 2A:
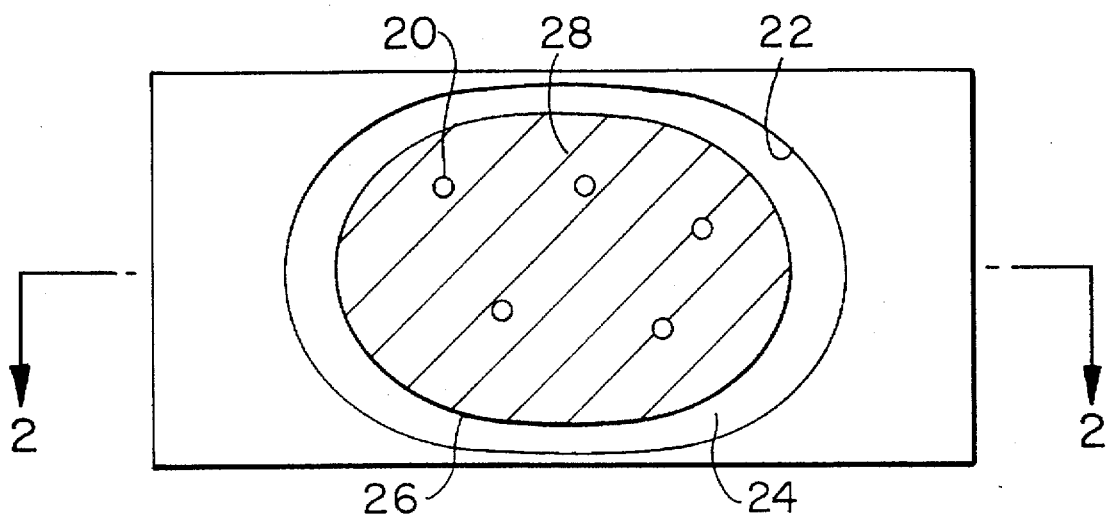
FIGS. 2a and 2b provide a schematic plan view and a cross-sectional illustration, respectively, of a patch of synthetic cartilage prepared in a pre-shaped well in accordance with the invention.
Figure 2B:
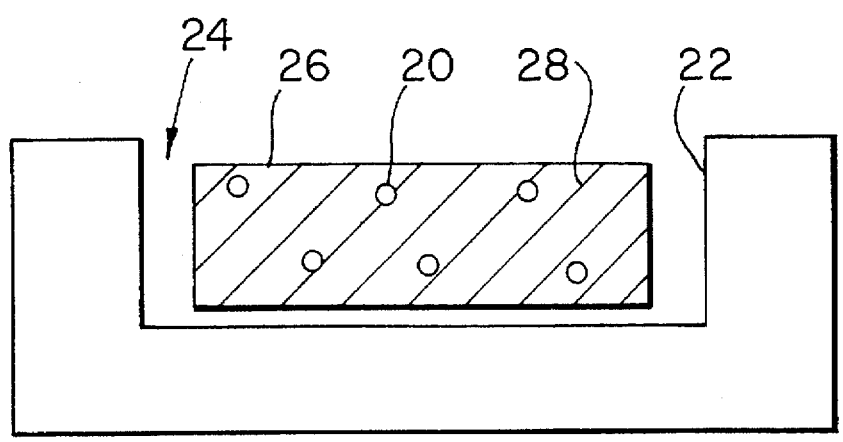

FIG. 2a is a schematic top plan view of a patch of synthetic cartilage (26) prepared in a pre-shaped well (24) in accordance with the invention. FIG. 2b is a schematic cross-sectional view of the patch of cartilage in the well of FIG. 1 taken at lines 2–2. Particulars of methods for making and using the synthetic cartilage are set forth in detail below.

I. Isolation of Tissue Containing Chondrogenic Cells

Chondrogenic cells useful in the practice of the instant invention may be sampled from a variety of sources in a mammal that contain such cells, for example, pre-existing cartilage tissue, perichondrial tissue or bone marrow.

Although costal cartilage, nasal cartilage, auricular cartilage, tracheal cartilage, epiglottic cartilage, thyroid cartilage, arytenoid cartilage and cricoid cartilage are useful sources of chondrogenic cells, articular cartilage (from either weight bearing or non-weight bearing joints) is the preferred source. Biopsy samples of articular cartilage may be readily isolated by a surgeon performing arthroscopic or open joint surgery. Procedures for isolating biopsy tissues are well known in the art and so are not described in detailed herein. See for example, "Operative Arthroscopy" (1991) by McGinty et al.,; Raven Press, New York, the disclosure of which is incorporated by reference herein.

Perichondrial tissue is the membranous tissue that coats the surface of all types of cartilage, except for articular cartilage. Perichondrial tissue provides nutrients to the chondrocytes located in the underlying unvascularized cartilage tissue. Perichondrial tissue sampled from costal (rib) cartilage of patients suffering from osteoporosis provides a source of chondrogenic cells when the normal articular cartilage is diseased or unavailable. Biopsy samples of perichondrial tissue may be isolated from the surface of costal cartilage or alternatively from the surface of auricular cartilage, nasal cartilage and cricoid cartilage using simple surgical procedures well known in the art. See for example: Skoog et al. (1990) *Scan. J. Plast. Reconstr. Hand Surg.* 24:89–93; Bulstra et al. (1990) *J. Orthro. Res.* 8:328–335; and Homminga et al. (1990) *J. Bone Constr. Surg.* 72:1003–1007, the disclosures of which are incorporated by reference herein.

It is contemplated also that chondrogenic cells, specifically mesenchymal cells, useful in the practice of the invention may be isolated from bone marrow. Surgical procedures useful in the isolation of bone marrow are well known in the art and so are not described in detailed herein. See for example, Wakitani et al. (1994) *J. Bone Joint Surg.* 76: 579–591, the disclosure of which is incorporated by reference herein.

II. Preparation of Denuded Chondrogenic Cells

Protocols for preparing denuded chondrogenic cells from cartilage tissue, perichondrial tissue, and bone marrow are set forth below.

A. From Articular Cartilage

Articular cartilage, both loaded (weight bearing) and unloaded (non-weight bearing), maybe be subjected to enzymatic treatment in order to disaggregate the tissue and release denuded chondrogenic cells from the extracellular matrix. Solutions containing proteolytic enzymes, for example, chondroitinase ABC, hyaluronidase, pronase, collagense, or trypsin may be added to articular cartilage tissue in order to digest the extracellular matrix. See for example, Watt & Dudhia (1988) *Differentiation* 38:140–147, the disclosure of which is incorporated herein by reference.

In a preferred procedure, articular cartilage is initially cut into pieces of about 1 mm in diameter, or less. This is routinely performed using a sterile scalpel. The minced tissue then is disaggregated enzymatically, for example, by the addition of a solution containing 0.1% collagenase (Boehringer Mannheim GmbH, Germany). Approximately 1 ml of collagenase is added per 0.25 ml equivalents of minced tissue. The sample is then mixed and incubated overnight (up to 16 hours) at 37° C., with agitation. Following the overnight digestion, the residual pieces of tissue are harvested by centrifugation, the supernatant removed, and the remaining cartilage pieces redigested by the addition of a solution containing, for example, 0.25% collagenase and 0.05% trypsin (Sigma Chemical Co., St. Louis). Approximately 1 ml of 0.25% collagenase, 0.05% trypsin is added per 0.25 ml equivalents of residual tissue. The sample then is mixed and incubated for 2–4 hours at 37° C., with agitation. Any remaining tissue is pelleted by centrifugation and the cell suspension harvested. The collagenase, trypsin step is repeated 2–4 times or until the tissue is completely disaggregated.

The enzymatic reaction is terminated by the addition of tissue culture medium supplemented with approximately 10% fetal bovine serum (FBS) (Hyclone, Logan, Utah). A preferred cell culture medium includes, for example, Dulbecco's minimal essential medium (DMEM) (Sigma Chemical Co., St. Louis) supplemented with 10% FBS. An alternative cell culture medium includes a 1:1 (vol/vol) mixture of Medium 199 (Sigma Chemical Co., St. Louis) and Molecular Cell Developmental Biology Medium 202 (MCDB 202) (Sigma Chemical Co., St. Louis), respectively, supplemented with 10% FBS. Alternatively, another cell culture medium useful in the practice of the invention includes a 3:1 (vol/vol) mixture of DMEM and Ham's F-12 (F12) (Sigma Chemical Co., St. Louis), respectively, supplemented with 10% FBS. Fractions containing denuded chondrogenic cells are combined, and the cells inoculated into a cell culture dish at a plating density of about $1\times10^2$–$5\times10^5$ cells/cm$^2$, preferably about $5\times10^2$–$1\times10^5$ cells/cm$^2$, and most preferably about $1\times10^3$–$1\times10^4$ cells/cm$^2$, for cell expansion and testing.

Chondrocytes may be isolated from costal cartilage, nasal cartilage, auricular cartilage, tracheal cartilage, epiglottic cartilage, thyroid cartilage, arytenoid cartilage and cricoid cartilage using the aforementioned procedure.

B. From Perichondrial Tissue

Denuded chondrogenic cells preferably are isolated from perichondrial tissue using the same procedure as described in section II A. hereinabove.

Briefly, the tissue is minced into pieces of about 1 mm in diameter, or less. The minced tissue is repeatedly digested with proteolytic enzymes, for example, trypsin and collagenase. The resulting denuded cells are inoculated into a cell culture dish at a plating density of about $1\times10^2$–$5\times10^5$ cells/cm$^2$, preferably about $5\times10^2$ to $1\times10^5$ cells/cm$^2$, and most preferably about $1\times10^3$–$1\times10^4$ cells/cm$^2$ for cell expansion and testing.

Alternatively, a non-destructive procedure may be used to isolate chondrogenic cells from perichondrial tissue. In this procedure, intact explant tissue is placed in a cell culture dish and incubated in growth medium. The chondrogenic cells located within the tissue migrate out of the tissue and onto the surface of the tissue plate where they begin to proliferate. See for example, Bulstra et al. (1990) *J. Orthop. Res.* 8:328–335, the disclosure of which is incorporated by reference herein. Briefly, pieces of the minced explant tissue are placed into a tissue culture plate containing tissue culture medium. A preferred cell culture medium comprises DMEM supplemented with 10% FBS. The explant tissues are incubated at 37° C., 5% $CO_2$ for 3–7 days. During this time the chondrogenic cells migrate out of the explant tissue and onto the surface of the tissue culture dish. After reattaching to the surface of the plate, the cells start to proliferate again.

C. From Bone Marrow

Chondrogenic cells, specifically mesenchymal cells, may be isolated from samples of bone marrow. Procedures useful for the isolation of mesenchymal cells from bone marrow are well known in the art, see for example: U.S. Pat. Nos. 5,197,985; 4,642,120; and Wakitani et al. (1994, supra).

For example, in a preferred method, a plug of bone marrow may be removed surgically from the mammal of interest and added to cell culture medium. Preferred complete growth media are disclosed in U.S. Pat. No. 5,197,985. The mixture then is vortexed to break up the plug of tissue. The resulting suspension is centrifuged to separate bone marrow cells from large pieces of particulate matter i.e., bone fragments. The cells then are dissociated to give a single cell suspension by forcing the cells through a syringe fitted with a series of 16, 18, and 20 gauge needles. The cells then are plated out into a tissue culture plate at a cell density of about $1\times10^5$–$1\times10^6$ cells/cm$^2$ for selectively separating and/or isolating bone marrow derived mesenchymal cells from the remaining cells present in the suspension.

III. Expansion of Denuded Chondrogenic Cells In Vitro

Chondrogenic cells isolated from cartilage tissue, perichondrial tissue, or bone marrow using the methods described in section II hereinabove may be placed in monolayer culture for proliferative expansion. The process enables one to amplify the number of isolated chondrogenic cells. In principal, the artisan may produce essentially an unlimited number of chondrogenic cells and therefore essentially an unlimited amount of synthetic cartilage. It is appreciated, however, that during proliferative expansion the chondrogenic cells dedifferentiate and lose their ability to secrete cartilage specific extracellular matrix. A procedure to assay whether the undifferentiated cells still retain their chondrogenic potential is described hereinbelow.

A. Cell Proliferation

Protocols for proliferating cells by monolayer culture are well known in the art, see for example, Pollack (supra), and so are not described in detail herein.

Briefly, monolayer cultures are initiated by inoculating primary chondrogenic cells, isolated from either cartilage tissue or perichondrial tissue, into a cell culture dish at a plating density density of about $1\times10^2$–$5\times10^5$ cells/cm$^2$, more preferably about $5\times10^2$–$1\times10^5$ cells/cm$^2$ and most preferably about $1\times10^3$–$1\times10^4$ cells/cm$^2$. Chondrogenic cells that have undergone one or more cycles of passaging are also plated out at the same plating densities. Primary chondrogenic cells isolated from bone marrow are plated out into a tissue culture plate at a cell density of about $1\times10^5$–$1\times10^6$ cells/cm$^2$. Chondrogenic cells from bone marrow that have undergone one or more cycles of passaging are plated out at plating densities of about $1\times10^2$–$5\times10^5$ cells/cm$^2$, more preferably about $5\times10^2$–$1\times10^5$ cells/cm$^2$ and most preferably about $1\times10^3$–$1\times10^4$ cells/cm$^2$. The chondrogenic cells subsequently are cultured at 37° C., 5% $CO_2$ in cell culture medium.

A preferred cell culture medium comprises DMEM supplemented with 10% FBS. Alternatively, a cell culture medium comprising a 1:1 (vol/vol) mixture of Medium 199 and MCDB 202, respectively, supplemented with 10% FBS may be used. Still another cell culture medium useful in the practice of the invention comprises a 3:1 (vol/vol) mixture of DMEM and F12, respectively, supplemented with 10% FBS.

Once the cell cultures become confluent, i.e., the cells grow to such a density on the surface of the plate that they contact one another, the cells are passaged and inoculated into a new plate. This may be accomplished by initially removing the cell culture medium overlaying the cells monolayer by aspiration, and washing the cell monolayer with phosphate buffered saline (PBS). The PBS is removed, by aspiration, and a solution containing a proteolytic enzyme, i.e., 0.1% trypsin, then is poured onto the monolayer. The proteolytic enzyme hydrolyzes proteins that anchor the cells onto the surface of the plate thereby releasing the cells from the surface of the plate. The proteolytic enzyme in the cell suspension then is inactivated by adding FBS to the suspension to give a final concentration of 10% (vol/vol). The density of cells in the suspension then is estimated and the cells re-plated into a new cell culture plate at a density of about $1\times10^2$–$5\times10^5$ cells, more preferably about $5\times10^2$–$1\times10^5$ cells, and most preferably about $1\times10^3$–$10^4$ cells per cm$^2$. The passaging procedure may be repeated multiple times, for example up to about 7 to 10 times, until enough cells have been propagated to prepare a piece of cartilage of pre-determined size.

It is appreciated that suspensions of proliferated cells may be cryopreserved indefinitely using techniques well known in the art. See for example, Pollack (supra). Accordingly, populations of chondrogenic cells may be stored for subsequent use whenever a necessity arises.

B. Assay To Measure Chondrogenic Potential of Proliferated Cells

Undifferentiated chondrogenic cells, expanded in monolayer culture, may be assayed to determine whether they still retain their chondrogenic potential. This may be performed by culturing the cells in a semi-solid medium in a process called agarose culture. This procedure is described in Benya et al. (1982) *Cell* 30:215–224, the disclosure of which is incorporated by reference herein.

Briefly, proliferated chondrogenic cells are seeded into a solution of warm 2% low melting temperature agarose (LT agarose) (BioRad, Richmond, Calif.). The use of LT agarose permits cells to be seeded into the agarose without thermal damage to the cells. The agarose is cooled to about 39°–41° C. prior to the addition of cells. Approximately $1\times10^3$–$1\times10^6$ cells are seeded into 1 ml of the liquid agarose.

The cells are cultured subsequently at 37° C., 5% $CO_2$ for 3–4 weeks in a cell culture medium preferably containing DMEM supplemented with 10% FBS. During this time, the chondrogenic cells replicate to from colonies which start to secrete an extracellular matrix. The resulting colonies have the appearance of small "nodules" embedded within the agarose. The colonies may be counted and the chondrogenic proportion of cells determined histochemically and immunohistochemically using procedures well known in the art.

Histochemical Staining

Briefly, agarose gels containing the cells are fixed with 10% formalin in PBS. The samples then are sectioned into 8–18 μm sections with a cryo-cut microtome (American Optical). General cellular morphology and tissue phenotype may be assessed by staining the section by the hematoxylin-eosin method well known in the art. Briefly, the resulting section is incubated in a stain comprising hematoxylin dissolved in 5% ethanol for 10 minutes. The section then is washed with water and incubated subsequently in an stain containing 1% eosin in 70% ethanol for 45 seconds. The sections then are washed with 95% ethanol. The nodules of extracellular matrix stain purple under these experimental conditions.

Sulfated proteoglycans in the extracellular matrix may be visualized by incubating the agarose particles in a stain comprising 1% alcian blue in 0.1N hydrochloric acid for 15–30 minutes. Alternatively, proteoglycans may be visualized by incubating the agarose particles in a stain comprising 0.2% safranin O/fast green in 1% acetic acid for 15–30 minutes. The stained particles then are washed with water. Sulfated proteoglycans present in the extracellular matrix stain blue and orange, by the two methods, respectively.

Immunohistochemical Staining

The agarose particles containing the chondrogenic cells are sectioned into 8–18 μm sections with a cryo-cut microtome (American Optical). The sections then are enzymatically digested in order to expose antigenic epitopes present on the extracellular matrix. A preferred enzyme includes the proteolytic enzyme protease type XIV (Sigma Chemical Co., St. Louis). Briefly, the agarose sections are incubated for 90 minutes at room temperature in Tris buffered saline, pH 7.4 (TBS) containing 0.4 mg/ml of protease type XIV. The resulting section then is washed twice with TBS.

Monoclonal antibodies that bind: link protein (8A4 from Hybridoma Bank, Baltimore, Md.); type I collagen (AB745 and MAB1340 from Chemicon International, Timacula, Calif.); type II collagen (PS48 from SanBio Inc., Amsterdam, Holland; CIICI from Hybridoma Bank, Baltimore, Md.); and chondroitin-6-sulfate (MabCs-D from Seikagaku America Inc, Rockville, Md.) may be used to detect the presence of these extracellular components in the agarose particles. Immunostaining may be performed using the VECTASTAIN ABC-AP kit (Vector Laboratory) pursuant to the manufacturers instructions.

IV. Preparation of Synthetic Cartilage Patch

Following proliferation, the chondrogenic cells still having chondrogenic potential are cultured in an anchorage-independent manner, i.e., in a well having a cell contacting, cell abhesive surface, in order to stimulate the secretion of cartilage-specific extracellular matrix components.

Heretofore, it has been observed that chondrogenic cells proliferatively expanded in an anchorage-dependent manner usually dedifferentiate and lose their ability to secrete cartilage-specific type II collagen and sulfated proteoglycan (Schlitz et al., supra; Mayne et al., supra; Mayne et al., supra; Okayama et al., supra; Pacifici & Holtzer, supra; Pacifici et al., supra; West et al., supra; von der Mark, supra; Oegama & Thompson, supra; Benya & Schaffer, supra). It has been discovered and disclosed herein that undifferentiated chondrogenic cells, when seeded into, and cultured in a well having a cell contacting surface that discourages adhesion of cells to the cell contacting surface, redifferentiate and start to secrete cartilage-specific collagen and sulfated proteoglycans thereby to form a patch of synthetic cartilage in vitro.

In addition, it has been found that culturing the cells in a pre-shaped well, enables one to manufacture synthetic cartilage patches of pre-determined thickness and volume. It is appreciated, however, that the volume of the resulting patch of cartilage is dependent not only upon the volume of the well but also upon the number of chondrogenic cells seeded into the well. Cartilage of optimal pre-determined volume may be prepared by routine experimentation by altering either, or both of the aforementioned parameters.

A. Preparation of Pre-shaped Well

Several approaches are available for preparing pre-shaped wells with cell contacting, cell abhesive surfaces.

The cell contacting surface of the well may be coated with a molecule that discourages adhesion of chondrogenic cells to the cell contacting surface. Preferred coating reagents include silicon based reagents i.e., dichlorodimethylsilane or polytetrafluoroethylene based reagents, i.e., Teflon®. Procedures for coating materials with silicon based reagents, specifically dichlorodimethylsilane, are well known in the art. See for example, Sambrook et al. (1989) "*Molecular Cloning A Laboratory Manual*", Cold Spring Harbor Laboratory Press, the disclosure of which is incorporated by reference herein. It is appreciated that other biocompatible reagents that prevent the attachment of cells to the surface of the well may be useful in the practice of the instant invention.

Alternatively, the well may be cast from a pliable or moldable biocompatible material that does not permit attachment of cells per se. Preferred materials that prevent such cell attachment include, but are not limited to, agarose, glass, untreated cell culture plastic and polytetrafluoroethylene, i.e., Teflon®. Untreated cell culture plastics, i.e., plastics that have not been treated with or made from materials that have an electrostatic charge are commercially available, and may be purchased, for example, from Falcon Labware, Becton-Dickinson, Lincoln Park, N.J. The aforementioned materials, however, are not meant to be limiting. It is appreciated that any other other pliable or moldable biocompatible material that inherently discourages the attachment of chondrogenic cells may be useful in the practice of the instant invention.

The size and shape of the well may be determined by the size and shape of the articular cartilage defect to be repaired. For example, it is contemplated that the well may have a cross-sectional surface area of 25 $cm^2$. This is the average cross-sectional surface area of an adult, human femoral chondyle. Accordingly, it is anticipated that a single piece of synthetic cartilage may be prepared in accordance with the invention in order to resurface the entire femoral chondyle. The depth of the well is preferably greater than about 0.3 cm and preferably about 0.6 cm in depth. The thickness of natural articular cartilage in an adult articulating joint is usually about 0.3 cm. Accordingly, the depth of the well should be large enough to permit a cartilage patch of about 0.3 cm to form. However, the well should also be deep enough to contain growth medium overlaying the cartilage patch.

It is contemplated also that a large piece of cartilage prepared in accordance with the invention may be "trimmed" to a pre-selected size and shape by a surgeon performing surgical repair of the damaged cartilage. Trimming may be performed with the use of a sharp cutting implement, i.e., a scalpel, a pair of scissors or an arthroscopic device fitted with a cutting edge, using procedures well known in the art.

The pre-shaped well preferably is cast in a block of agarose gel under aseptic conditions. Agarose is an economical, biocompatible, pliable and moldable material that can be used to cast pre-shaped wells, quickly and easily. As mentioned above, the dimensions of the well may dependent upon the size of the resulting cartilage plug that is desired.

A pre-shaped well may be prepared by pouring a hot solution of molten LT agarose (BioRad, Richmond, Calif.) into a tissue culture dish containing a cylinder. The cylinder having dimensions that mirror the shape of the well to be formed. The size and shape of the well may be chosen by the artisan and may be dependent upon the shape of the articular cartilage defect to be repaired. Once the agarose has cooled and solidified around the cylinder, the cylinder is carefully removed with forceps. The surface of the tissue culture dish that is exposed by the removal of the cylinder is covered with molten agarose. This seals the bottom of the well and provides a cell abhesive surface at the base of the well. When the newly added molten LT agarose cools and solidifies, the resulting pre-shaped well is suitable for culturing, and stimulating the redifferentiation of proliferated chondrogenic cells. It is appreciated, however, that alternative methods may be used to prepare a pre-shaped well useful in the practice of the invention.

B. Growth of Cartilage Patch

Proliferated chondrogenic cells in suspension (from section III A, hereinabove) subsequently are seeded into and cultured in the pre-shaped well. The cells are diluted by the addition of cell culture medium to a cell density of about $1 \times 10^5 - 1 \times 10^9$ proliferated chondrogenic cells per ml, or more preferably about $1 \times 10^6 - 5 \times 10^8$ cells per ml, and most preferably about $3 \times 10^6 - 2 \times 10^8$ cells per ml. A preferred cell culture medium comprises DMEM supplemented with 10% FBS. Alternatively, a cell culture medium comprising a 1:1 (vol/vol) mixture of Medium 199 and MCDB 202, respectively, supplemented with 10% FBS may be used. Still another cell culture medium useful in the practice of the invention comprises a 3:1 (vol/vol) mixture of DMEM and F12, respectively, supplemented with 10% FBS.

About, $1 \times 10^3 - 1 \times 10^7$ cells, preferably $1 \times 10^4 - 1 \times 10^6$ cells, and most preferably about $5 \times 10^4 - 5 \times 10^5$ cells produce a piece of synthetic cartilage 1 mm$^3$ in volume. Accordingly, the artisan may produce a patch of synthetic cartilage of pre-determined size by seeding an appropriate number of chondrogenic cells into a pre-shaped well. The cells subsequently are cultured at 37° C., 5% $CO_2$, for 1 to 90 days, preferably 5 to 60 days, and most preferably 10 to 30 days in order to permit secretion of cartilage-specific type II collagen and sulfated proteoglycans thereby to form of synthetic cartilage in vitro. The cell culture medium is removed from the well and replaced with fresh cell culture medium every other day in order to maintain optimal viability of the cells.

Within about four hours of seeding the proliferated chondrogenic cells into the well, the cells coalesce to form a cohesive plug of cells. The cells in the cohesive plug initially secrete type I collagen. After about 4–10 days, the cells start to secrete cartilage-specific sulfated proteoglycans and type II collagen. Over the same period of time, the level of type I collagen synthesis decreases. After prolonged periods of time in culture the collagen expressed by the chondrogenic cells in the well is predominantly type II collagen. It is contemplated however, that the cohesive plug of cells formed within four hours may be removed from the well and surgically implanted into the cartilage defect. It is anticipated that the undifferentiated chondrogenic cells subsequently may redifferentiate in situ thereby to form synthetic cartilage within the joint.

The resulting synthetic cartilage tissue formed in the pre-shaped well may be assayed, biochemically or morphologically, using the procedures described hereinabove prior to implantation into the joint. Briefly, the synthetic cartilage may be sectioned into 8–18 µm sections using a cryo-microtome (American Optical) and resulting sections stained using the procedures described in section III B.

It is contemplated that polypeptide growth factors may be added to the chondrogenic cells in the pre-shaped well to enhance or stimulate the production of articular cartilage specific proteoglycans and/or collagen (Luyten & Reddi (1992) in "Biological Regulation of the Chondrocytes", CRC Press, Boca Raton, Ann Arbor, London, and Tokyo, p.p. 227–236). Preferred growth factors include, but are not limited to transforming growth factor-β (TGF-β), insulin-like growth factor (IGF), platelet derived growth factor (PDGF), epidermal growth factor (EGF), acidic fibroblast growth factor (aFBF), basic fibroblast growth factor (bFBF), hepatocytic growth factor, (HGF) keratinocyte growth factor (KGF), the bone morphogenic factors (BMPs) i.e., BMP-1, BMP-2, BMP-3, BMP-4, BMP-5 and BMP-6 and the osteogenic proteins (OPs), i.e. OP-1, OP-2 and OP-3. Preferred concentrations of TGF-β, IGF, PDGF, EGF, aFBF, bFBF, HGF, and KGF, range from about 1 to 100 ng/ml, more preferably from about 5 to about 50 ng/ml, and most preferably from about 10 to about 20 ng/ml. Preferred concentrations of the BMP's and OP's range from about 1 to about 500 ng/ml, more preferably from about 50 to about 300 ng/ml, and most preferably from about 100 to about 200 ng/ml. However, these particular growth factors are not limiting. Any polypeptide growth factor capable of stimulating or inducing the production of cartilage specific proteoglycans and collagen may be useful in the practice of the instant invention.

In addition, it is contemplated that ascorbate may be added to the chondrogenic cells in the pre-shaped well to enhance or stimulate the production of cartilage specific proteoglycans and collagen. Preferred concentrations of ascorbate range from about 1 to about 1000 µg/ml, more preferably from about 20 to about 500 µg/ml, and most preferably from about 50 to about 100 µg/ml.

V. Surgical Repair of Articular cartilage Defect Cartilage defects in mammals are readily identifiable visually during arthroscopic examination or during open surgery of the joint. Cartilage defects may also be identified inferentially by using computer aided tomography (CAT scanning), X-ray examination, magnetic resonance imaging (MRI), analysis of synovial fluid or serum markers or by any other procedures known in the art. Treatment of the defects can be effected during an arthroscopic or open surgical procedure using the methods and compositions disclosed herein.

Accordingly, once the defect has been identified, the defect may be treated by the following steps of (1) surgically implanting at the pre-determined site, a piece of synthetic articular cartilage prepared by the methodologies described herein, and (2) permitting the synthetic articular cartilage to integrate into pre-determined site.

The synthetic cartilage patch optimally has a size and shape such that when the patch is implanted into the defect, the edges of the implanted tissue contact directly the edges of the defect. In addition, the synthetic cartilage patch may be fixed in placed during the surgical procedure. This can be effected by surgically fixing the patch into the defect with biodegradable sutures, i.e., (Ethicon, Johnson & Johnson) and/or by applying a bioadhesive to the region interfacing the patch and the defect. Preferred bioadhesives include, but are not limited to: fibrin-thrombin glues similar to those disclosed in Fr. Pat. No. 2 448 900; Fr. Pat. No. 2 448 901 and EP.S.N. 88401961.3 and synthetic bioadhesives similar to those disclosed in U.S. Pat. No. 5,197,973. It is contemplated, however, that alternative types of sutures and biocompatible glues may be useful in the practice of the invention.

In some instances, damaged articular cartilage maybe surgically excised prior the to implantation of the patch of synthetic cartilage. Additionally, the adhesion of the synthetic cartilage patch to the articular cartilage defect may be enhanced by treating the defect with transglutaminase (Ichinose et al. (1990) *J. Biol. Chem.* 265(3):13411–13414; Najjar et al. (1984) in "*Transglutaminases*", Boston, Martinuse-Nijhoff). Initially, the cartilage defect is dried, for example by using cottonoid, and filled with a solution of transglutaminase. The solution is subsequently removed, for example, by aspiration, leaving a film containing transglutaminase upon the cartilage. The synthetic cartilage patch is implanted subsequently into the defect by the methods described above.

The synthetic cartilage patches preferably are allogeneic, and most preferably autogenic nature. Accordingly, synthetic allogeneic cartilage may be prepared from biopsy tissue isolated from a mammal belonging to the same species as the intended recipient. Synthetic autogenic cartilage may be prepared from biopsy tissue derived from the intended recipient.

In addition the synthetic cartilage may be useful in the repair of human articular cartilage defects. Accordingly, chondrogenic cells may be isolated from: human cartilage tissue, i.e, human articular cartilage (from weight-bearing and non-weight bearing joints), human costal cartilage, human nasal cartilage, human auricular cartilage, human tracheal cartilage, human epiglottic cartilage, human thyroid cartilage, human arytenoid cartilage and human cricoid cartilage; from human perichondrial tissue, i.e., perichondrial tissue sampled from the surface of human costal cartilage, human nasal cartilage, human auricular cartilage, human tracheal cartilage, human epiglottic cartilage, human thyroid cartilage, human arytenoid cartilage and human cricoid cartilage; or from human bone marrow.

Surgical procedures for effecting the repair of articular cartilage defects are well known in the art. See for example: Luyten & Reddi (1992) in "*Biological Regulation of the Chondrocytes*", CRC Press, Boca Raton, Ann Arbor, London, & Tokyo, p.p. 227–236, the disclosure of which is incorporated by reference herein.

EXAMPLE I

Isolation and Expansion of Chondrogenic Cells from Perichondrial and Cartilage Tissue Samples of human perichondrial tissue (HPT) and dog perichondrial tissue (DPT) were obtained from the Department of Orthopedic Surgery at Brigham and Women's Hospital, Boston, Mass. Samples of human articular cartilage (HAC) and dog articular cartilage (DAC) were obtained from the Department of Orthopedic Surgery at Brigham and Women's Hospital, Boston, Mass. and from the Department of Pathology, Massachusetts General Hospital, Boston, Mass.

The tissues were minced finely and incubated overnight in a buffer solution containing 0.1% collagenase at 37° C., with agitation. Following the overnight digestion, the residual pieces of tissue were harvested, and digested further with a solution containing 0.25% collagenase and 0.05% trypsin for 2–4 hours 37° C. The collagenase, trypsin step was repeated for a total of three times and the fractions containing denuded chondrogenic cells combined, and plated out into a cell culture plate at a density of about $1 \times 10^3 – 1 \times 10^4$ cells per cm$^2$ of the plate.

The cells were cultured at 37° C., 5% $CO_2$ in a medium containing DMEM supplemented with 10% FBS. When the cellular monolayers became confluent, the cells were washed three times with PBS and removed from the surface of the plate by adding a solution containing 0.05% trypsin to the monolayer. The trypsin was inactivated by the addition of 10% FBS to the suspension of cells. The number of cells in the single cell suspension were counted, re-plated, proliferated and repassaged until use.

The proliferated chondrogenic cells were shown to maintain their chondrogenic potential by culturing them in semi-solid agarose medium (Benya et al. (1982), supra). The proliferated cells were seeded into 2% LT agarose at a cell density of about $1 \times 10^3 – 1 \times 10^6$ cells per ml of liquid agarose. Then, the cells were cultured at 37° C. for 21–35 days, as specified below, in a medium containing DMEM and 10% FBS. The colonies gave the appearance of small "nodules" in agarose. The controls were chondrogenic cells that were grown as monolayers but not cultured in agarose culture.

The composition of the resulting particles was assayed by histochemical staining. The resulting particles were first fixed with 10% formalin in PBS. The cellular morphology and tissue phenotype was assessed by staining a section of the agarose gel with hematoxylin/eosin. The presence of sulfated proteoglycans in the extracellular matrix was assayed by staining the particles with 1% alcian blue in hydrochloric acid.

The presence of type I and type II collagen in the particles was assayed immunohistochemically using the: anti-type I collagen monoclonal antibodies AB745 and MAB1340; and the anti-type II collagen monoclonal antibodies PS48 and CIICI in combination with the VECTASTAIN ABC-AP immunodetection kit (Vector Laboratory).

The results of the morphological and histochemical assays are summarized in TABLE I, below. The presence and absence of type I collagen, type II collagen, and sulfated proteoglycans are represented by + and –, respectively.

TABLE I

| Source of Chondrogenic Cells | Type I Collagen | Sulfated Proteoglycan | Type II Collagen |
| --- | --- | --- | --- |
| DPT | | | |
| 21 days | + | + | – |
| 35 days | + | + | + |

TABLE I-continued

| Source of Chondrogenic Cells | Type I Collagen | Sulfated Proteoglycan | Type II Collagen |
|---|---|---|---|
| HAC | | | |
| 21 days DAC | + | + | + |
| 21 days HAC | + | + | + |
| (monolayer) DAC | + | – | – |
| (monolayer) | + | – | – |

The results show that chondrogenic cells can be isolated from mammalian perichondrial tissue and cartilage. The cells also maintain their chondrogenic potential following proliferation as monolayers.

EXAMPLE II

Preparation of a Pre-shaped Well Having a Cell Contacting, Cell Abhesive Surface It is appreciated that the size of the well may be dependent upon the size of the piece of cartilage required. The wells prepared herein were formed in LT agarose. 2 ml of a hot 2% agarose solution (not containing any cells) was poured into a tissue culture dish (35 mm in diameter) having a cylinder (3–5 mm, outside diameter) resting in the center of the dish. After the agarose solidified around the cloning cylinder (5–10 minutes), the cylinder was carefully removed with forceps. The exposed surface of the tissue culture dish resulting from the removal of the cloning cylinder was completely covered by the addition of a further 50–100 µl of hot, liquid 2% agarose.

EXAMPLE III

Preparation of Synthetic Articular Cartilage Patches In Vitro

Another batch of proliferated chondrogenic cells prepared in accordance with Example I were subsequently seeded as replicate samples into wells prepared as described in Example II. The cells were either passaged twice (2°) or three times (3°), as specified below, prior to seeding them into agarose wells. Approximately, $1 \times 10^6$ proliferated chondrogenic cells were seeded into the pre-shaped wells. The cells were cultured for 14 days at 37° C., 5% $CO_2$ in growth medium containing DMEM supplemented with 10% FBS.

The cells seeded into the agarose well were unable to attach to the surface of the well. The chondrogenic cells, deprived of anchorage, interacted with one another and coalesced within about four hours to generate a cohesive plug of cells. The chondrogenic cells began to differentiate, as judged by the production of articular cartilage specific markers. After 14 days in culture, the cohesive plugs of cells were assayed morphologically and histochemically. The controls were chondrogenic cells that were grown as monolayers but not cultured in the pre-shaped wells.

The resulting patches and cellular monolayers were first fixed with 10% formalin in PBS. The cellular morphology and tissue phenotype were assessed by staining a section of the patch with hematoxylin/eosin. The presence of sulfated proteoglycans in the extracellular matrix was assayed by staining the remaining sections of the patches with either 1% alcian blue in hydrochloric acid or 0.2% safranin O/fast green.

The presence of type I and type II collagen in the particles was assayed immunohistochemically using the: anti-type I collagen monoclonal antibodies AB745 and MAB1340; and the anti-type II collagen monoclonal antibodies PS48 and CIICI in combination with the VECTASTAIN ABC-AP immunodetection kit (Vector Laboratory).

The results of the morphological and histochemical assays are summarized in TABLE II, below. The presence and absence of type I collagen, type II collagen, and sulfated proteoglycans are represented by + and –, respectively.

TABLE II

| Source of Chondrogenic Cells | Type I Collagen | Sulfated Proteoglycan | Type II Collagen |
|---|---|---|---|
| HPT (2°) | + | + | + |
| DPT (2°) | + | + | + |
| DAC (3°) | + | + | + |
| HAC (monolayer) | + | – | – |
| DAC (monolayer) | + | – | – |

The results in TABLE II show that synthetic articular cartilage can be formed in vitro using chondrogenic cells that have been proliferated previously in an undifferentiated state as cellular monolayers.

EXAMPLE IV

Preparation of Synthetic Articular Cartilage Patches of Pre-determined Volume Different numbers of chondrogenic cells derived from human and dog articular cartilage and from human perichondrial tissue cartilage as prepared in Example I were seeded into pre-shaped wells as prepared in Example II. The cells were cultured for four days at 37° C., 5% $CO_2$ in growth medium containing DMEM supplemented with 10% FBS.

After 4 days in culture the patches were removed from the wells and the thickness and volume of the patches determined. The results are summarized below in TABLE III.

TABLE III

| (A) Chondrogenic Cells From Human Articular Cartilage | | |
|---|---|---|
| Cell Number | Diameter of patch (mm) | Volume of patch (mm³) |
| a) $1 \times 10^5$ | 1.0 | 0.8 |
| b) $5 \times 10^5$ | 2.0 | 3.1 |
| c) $1.5 \times 10^6$ | 2.5 | 4.9 |
| (B) Chondrogenic Cells From Dog Articular Cartilage | | |
| a) $1 \times 10^5$ | 0.5 | 0.2 |
| b) $5 \times 10^5$ | 1.0 | 0.8 |
| c) $1.5 \times 10^6$ | 2.0 | 3.1 |
| d) $5 \times 10^6$ | 3.0 | 7.1 |
| (C) Chondrogenic Cells From Dog Perichondrial Tissue | | |
| a) $1 \times 10^5$ | 0.5 mm | 0.2 |
| b) $5 \times 10^5$ | 1.0 mm | 0.8 |
| c) $5 \times 10^6$ | 2.5 mm | 4.9 |

The results in Table III demonstrate that the volume of the resulting cartilage patches can be experimentally controlled by adjusting the number of cells seeded into the pre-shaped well.

The invention may be embodied in other specific forms without departing from the spirit or essential characteristics thereof. The present embodiments are therefore to be considered illustrative and not restrictive, the scope of the invention being indicated by the appended claims rather than by the foregoing description, and all changes which come within the meaning and range of equivalency of the claims are therefore intended to be embraced therein.

What is claimed is:

1. A method for repairing an articular cartilage defect at a pre-determined site in a mammal, the method comprising the steps of:
   (a) surgically implanting at the predetermined site of said defect a piece of synthetic cartilage of a predetermined volume prepared by the method comprising:
      (i) seeding denuded chondrogenic cells, proliferated ex vivo, into a preshaped well having a cell contacting, cell abhesive surface, said well being dimensioned to provide a predetermined volume of the synthetic cartilage so that said volume approximates a volume of the cartilage defect to be repaired;
      (ii) culturing said cells in said well for a time sufficient to permit said cells to differentiate and form a synthetic cartilage comprising chondrogenic cells dispersed within an endogenously produced extracellular matrix;
      (iii) removing said synthetic cartilage from said well; and
   (b) permitting the synthetic cartilage to integrate into the predetermined site.

2. The method of claim 1, comprising an additional step of fixing said synthetic cartilage at said pre-determined site.

3. The method of claim 2, wherein said additional step comprises surgically fixing said synthetic cartilage at said pre-determined site.

4. The method of claim 2, wherein said additional step comprises applying a bioadhesive to the interface of said pre-determined site and said synthetic cartilage.

5. The method of claim 1, wherein said method comprises the additional step of excising defective articular cartilage from said site prior to implanting the synthetic cartilage.

6. The method of claim 1, wherein step (a) is effected by implanting a plurality of synthetic cartilage pieces at said site.

7. The method of claim 1, wherein said defect is a partial thickness defect.

8. The method of claim 1, wherein said synthetic cartilage is autogenic or allogeneic.

9. A method for repairing an articular cartilage defect at a pre-determined site in a mammal, the method comprising the steps of:
   (a) surgically implanting at the predetermined site of said defect a piece of synthetic cartilage of a pre-determined volume prepared by the method comprising:
      (i) providing a tissue comprising interconnected chondrogenic cells;
      (ii) disaggregating said tissue to release denuded cells;
      (iii) proliferating said denuded cells ex vivo;
      (iv) seeding said proliferated cells into a preshaped well having a cell contacting, cell abhesive surface, said well being dismensioned to provide a predetermined volume of the synthetic cartilage so that said volume approximates a volume of the cartilage defect to be repaired;
      (v) culturing said cells in said well for a time sufficient to permit said cells to differentiate and form a formation of synthetic cartilage comprising chondrogenic cells dispersed within an endogenously produced extracellular matrix;
      (vi) removing said synthetic cartilage from said well; and
   (b) permitting the synthetic cartilage to integrate into the pre-determined site.

10. A method for repairing an articular cartilage defect at a predetermined site in a mammal, the method comprising the steps of:
    (a) surgically implanting at the predetermined site of said defect a piece of synthetic cartilage of a pre-determined volume prepared by the method comprising:
       (i) seeding denuded chondrogenic cells, proliferated ex vivo, into a preshaped well having a cell contacting, cell abhesive surface, said well being dimensioned to provide a pre-determined volume of the synthetic cartilage so that said volume approximates a volume of the cartilage defect to be repaired;
       (ii) adding ascorbate to said cells in said well;
       (iii) culturing said cells in said well for a time sufficient to permit said cells to differentiate and form a synthetic cartilage comprising chondrogenic cells dispersed within an endogenously produced extracellular matrix;
       (iv) removing said synthetic cartilage from said well; and
    (b) permitting the synthetic cartilage to integrate into the predetermimined site.

11. The method of claims 1, 9 or 10, wherein said cell abhesive surface comprises a surface coated with silicon or polytetrafluoroethylene.

12. The method of claims 1, 9 or 10, wherein said well is defined by a material selected from the group consisting of agarose, glass, untreated cell culture plastic and polytetrafluoroethylene.

13. The method of claims 1, 9 or 10, wherein said chondrogenic cells are derived from cartilage.

14. The method of claims 1, 9 or 10, further comprising an additional step of adding a polypeptide growth factor selected from the group consisting of transforming growth factor -β, platelet derived growth factor, insulin-like growth factor, acidic fibroblast growth factor, basic fibroblast growth factor, epidermal growth factor, hepatocytic growth factor, keratinocyte growth factor, and bone morphogenic protein to the cells prepared by the method in step (a).

15. A method for repairing an articular cartilage defect at a pre-determined site in a mammal, the method comprising the steps of:
    (a) surgically implanting at the predetermined site of said defect a piece of synthetic cartilage of a predetermined volume prepared by the method consisting of:
       (i) seeding denuded chondrogenic cells, proliferated ex vivo, into a preshaped well having a cell contacting, cell abhesive surface, said well being dimensioned to provide a predetermined volume of the synthetic cartilage so that said volume approximates a volume of the cartilage defect to be repaired;
       (ii) culturing said cells in said well for a time sufficient to permit said cells to differentiate and form a synthetic cartilage consisting of chondrogenic cells dispersed within an endogenously produced extracellular matrix;
       (iii) removing said synthetic cartilage from said well; and
    (b) permitting the synthetic cartilage to integrate into the predetermined site.

* * * * *